United States Patent
Martin (10) Patent No.: US 9,408,672 B2
(45) Date of Patent: Aug. 9, 2016

(54) METHOD AND APPARATUS FOR FACILITATING ACCESS THROUGH A PATIENT TISSUE

(71) Applicant: David Z. Martin, Towson, MD (US)

(72) Inventor: David Z. Martin, Towson, MD (US)

(*) Notice: Subject to any disclaimer, the term of this patent is extended or adjusted under 35 U.S.C. 154(b) by 462 days.

(21) Appl. No.: 13/906,568

(22) Filed: May 31, 2013

(65) Prior Publication Data

US 2013/0324980 A1    Dec. 5, 2013

Related U.S. Application Data

(60) Provisional application No. 61/654,175, filed on Jun. 1, 2012.

(51) Int. Cl.
| | | |
|---|---|---|
| *A61B 90/50* | (2016.01) | |
| *A61B 17/00* | (2006.01) | |
| *A61B 17/3209* | (2006.01) | |
| *A61B 17/064* | (2006.01) | |
| *A61B 17/068* | (2006.01) | |
| *A61B 17/08* | (2006.01) | |
| *A61B 17/32* | (2006.01) | |

(52) U.S. Cl.
CPC ............ *A61B 90/50* (2016.02); *A61B 17/00* (2013.01); *A61B 17/0644* (2013.01); *A61B 17/0684* (2013.01); *A61B 17/085* (2013.01); *A61B 17/32093* (2013.01); *A61B 2017/320052* (2013.01)

(58) Field of Classification Search
CPC ...... A61B 17/15; A61B 17/17; A61B 17/085; A61B 2017/320056; A61B 2017/081; A61B 2017/085; A61B 17/151–17/158; A61B 17/32093; A61B 2017/320052; A61B 90/50

USPC ......... 30/286, 294; 227/139, 150; 606/1, 129, 606/130, 167–173, 176–178, 185, 215–219
See application file for complete search history.

(56) References Cited

U.S. PATENT DOCUMENTS

| | | | | |
|---|---|---|---|---|
| 2,932,296 A | * | 4/1960 | Sanders | 606/167 |
| 2,943,392 A | * | 7/1960 | Attridge | 30/310 |
| 3,698,395 A | | 10/1972 | Hasson | |
| 3,863,640 A | * | 2/1975 | Haverstock | 606/216 |
| 4,038,989 A | * | 8/1977 | Romero-Sierra et al. | 606/216 |
| 4,114,624 A | * | 9/1978 | Haverstock | 606/167 |
| 2006/0241691 A1 | * | 10/2006 | Wilk | 606/215 |
| 2013/0296930 A1 | * | 11/2013 | Belson et al. | 606/216 |

* cited by examiner

*Primary Examiner* — Todd E Manahan
*Assistant Examiner* — Charles Wei
(74) *Attorney, Agent, or Firm* — Taroli, Sundheim, Covell & Tummino LLP (57) ABSTRACT

A system for facilitating access through a substantially planar and laterally oriented patient skin surface includes a guiding substrate extending substantially parallel to the skin surface and selectively directly fastened thereto. The guiding substrate supports a guiding structure in a substantially fixed relationship to an access site of the skin surface. A tool carriage is configured to accept surgical tools for sequential interaction with the access site. The tool carriage engages the guiding structure such that the tool carriage is guided along a predetermined action path when motive force is provided to the tool carriage. The tool carriage is guided along the action path with an incising tool in penetrating contact with the access site of the skin surface to create a laterally elongate incision at the access site. The tool carriage is guided along the action path to substantially close the incision at the access site.

32 Claims, 7 Drawing Sheets

METHOD AND APPARATUS FOR FACILITATING ACCESS THROUGH A PATIENT TISSUE

RELATED APPLICATION

This application claims priority from U.S. Provisional Application No. 61/654,175, filed 1 Jun. 2012, the subject matter of which is incorporated herein by reference in its entirety.

TECHNICAL FIELD

The present invention relates to an apparatus and method for facilitating access through a patient tissue and, more particularly, to a method and apparatus for facilitating access through a patient skin surface.

BACKGROUND OF THE INVENTION

Many surgical procedures are performed through an incision in a patient's skin surface. The skin surface is cut, generally through the use of a hand-held scalpel blade, to produce a surgical wound/incision at a desired access site. The surgical incision is usually substantially linear, but because the cut is made free-hand, the incision may not be precisely located or shaped (e.g., there may be curved or curvilinear aspects to the incision), and may have differing cut depths along its length according to the varying pressure applied to the scalpel blade. The surgeon may also inadvertently make small angulations during this freehand incising, which "bevels" the incision edges and thereby contribute to healing delays and/or poor scar formation.

The surgical procedure is carried out in any desired manner, using the surgical incision for access. Once the invasive portion of the surgical procedure is complete, the surgeon begins approximating the surgical incision by pulling the incision edges together into alignment and placing sutures, clips, staples, adhesives, or other fasteners to hold the edges closed for healing. However, this portion of the access procedure is also generally accomplished manually and freehand, so the approximation and fastener placement are often uneven and/or imprecisely done, despite the best efforts of the surgeon. Also, despite an emphasis on incision edge eversion during surgeon training, advantageous contact between the deep dermis on both edges of the incision does not always occur during freehand incision approximation, thus potentially hindering healing of the surgical incision.

SUMMARY OF THE INVENTION

In an embodiment of the present invention, a system for facilitating access through a patient skin surface. The skin surface is substantially planar and laterally oriented. A guiding substrate extends substantially parallel to the skin surface and is selectively directly fastened thereto. The guiding substrate, when fastened to the skin surface, supports a guiding structure in a substantially fixed relationship to an access site of the skin surface. A tool carriage is configured to accept at least a chosen one of a plurality of surgical tools for sequential interaction with the access site. The tool carriage includes a following structure configured for selective engagement with the guiding structure such that the tool carriage is guided along a predetermined action path when the following structure and guiding structure are engaged and motive force is provided to the tool carriage. When the surgical tool is an incising tool, the tool carriage is guided along the action path with the incising tool in penetrating contact with the access site of the skin surface to create a laterally elongate incision at the access site, using the incising tool, and thereby provide access below the skin surface. When the surgical tool is a closure tool, the tool carriage is guided along the action path to substantially close the incision at the access site, using the closure tool, and thereby prevent access through the incision below the skin surface.

In an embodiment of the present invention, a method of facilitating access through a patient skin surface is provided. The skin surface is substantially planar and laterally oriented. A guiding substrate is directly fastened to the skin surface. The guiding substrate extends substantially parallel to the skin surface. A guiding structure is supported in a substantially fixed relationship to an access site of the skin surface with the guiding substrate. A tool carriage is configured to accept at least a chosen one of a plurality of surgical tools for sequential interaction with the access site. The tool carriage includes a following structure. The following structure is selectively engaged with the guiding structure. The tool carriage is guided along a predetermined action path when the following structure and guiding structure are engaged and motive force is provided to the tool carriage. When the surgical tool is an incising tool, the tool carriage is guided along the action path with the incising tool in penetrating contact with the access site of the skin surface to create a laterally elongate incision at the access site, using the incising tool, and thereby provide access below the skin surface. When the surgical tool is a closure tool, the tool carriage is guided along the action path to substantially close the incision at the access site, using the closure tool, and thereby prevent access through the incision below the skin surface.

In an embodiment of the present invention, a device for facilitating access through a patient skin surface is provided. The skin surface is substantially planar and laterally oriented. A pair of guiding rails are fastened to the skin surface. The guiding rails are laterally spaced along the skin surface with an access site on the skin surface interposed laterally between the guiding rails. At least one tool carriage is configured to movably engage the guiding rails such that motive force exerted in the transverse direction upon the tool carriage causes the tool carriage to move, guided by the rails, in the transverse direction. An incision tool is selectively carried by a tool carriage and accordingly is guided by the movable engagement between the tool carriage and the guiding rails to create a transversely extending incision in the skin surface at the access site and thereby provide access through the skin surface. A closure tool is selectively carried by a tool carriage and accordingly guided by the movable engagement between the tool carriage and the guiding rails to close the incision in the skin surface at the access site and thereby substantially prevent access through the skin surface.

BRIEF DESCRIPTION OF THE DRAWINGS

For a better understanding of the invention, reference may be made to the accompanying drawings, in which.

DESCRIPTION OF EMBODIMENTS

Figure 1:
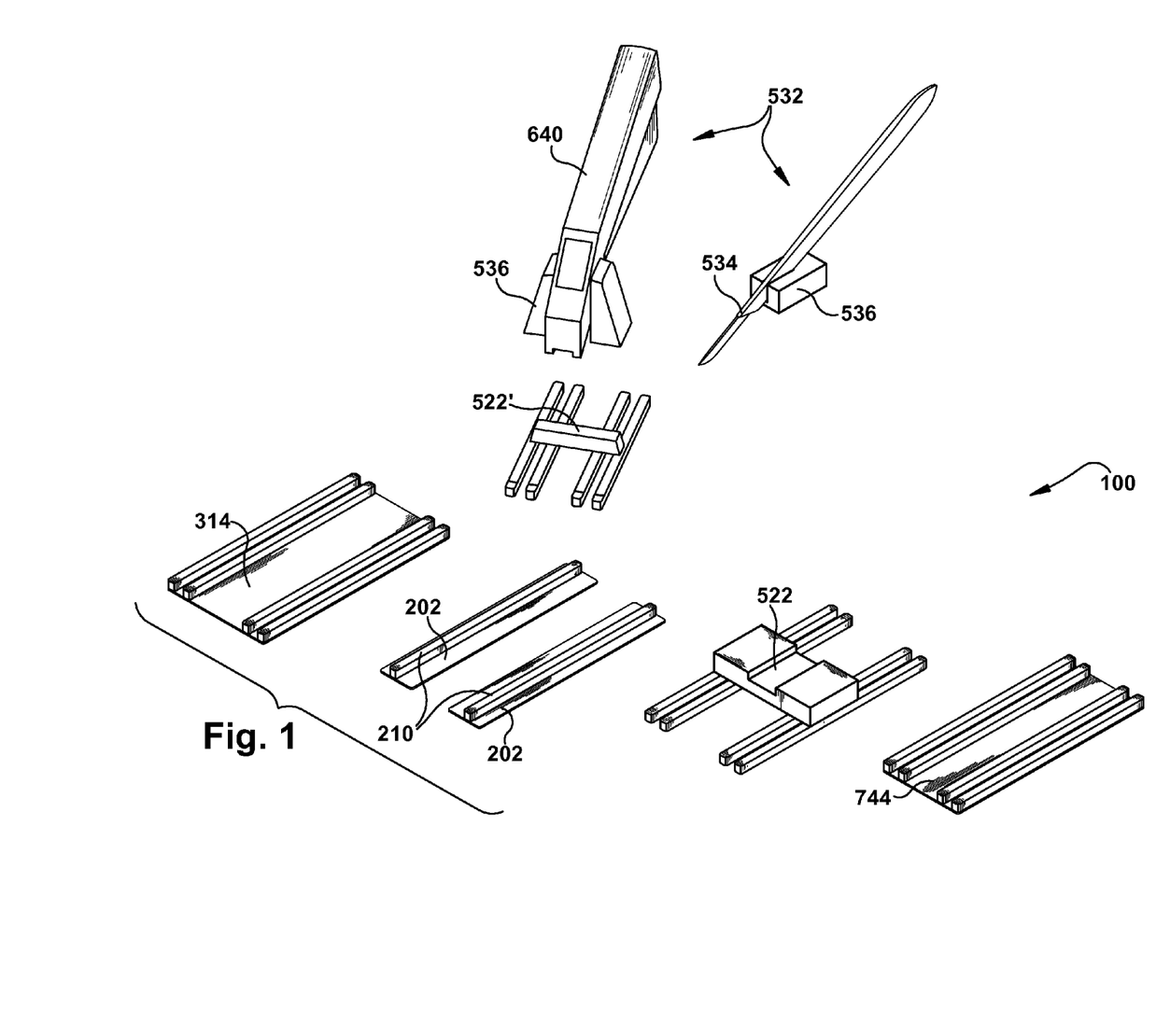
FIG. 1 is a top view of a plurality of components according to an embodiment of the present invention.

In accordance with the present invention, FIG. 1 depicts a plurality of components comprising an apparatus 100 for facilitating access through a patient tissue. The patient tissue will be discussed herein as substantially planar and laterally oriented—i.e., approximately coinciding with the plane of the page in FIG. 1. The patient tissue is shown and described herein at least as skin surface, but the patient tissue (and corresponding surgical procedure) could be any desired types such as, but not limited to, surface skin tissue, subsurface skin tissue, muscle tissue, nerve tissue, organ tissue, connective tissue, bone tissue, or any other suitable human, animal, or other patient tissue use environment for the present invention.

Figure 2A:
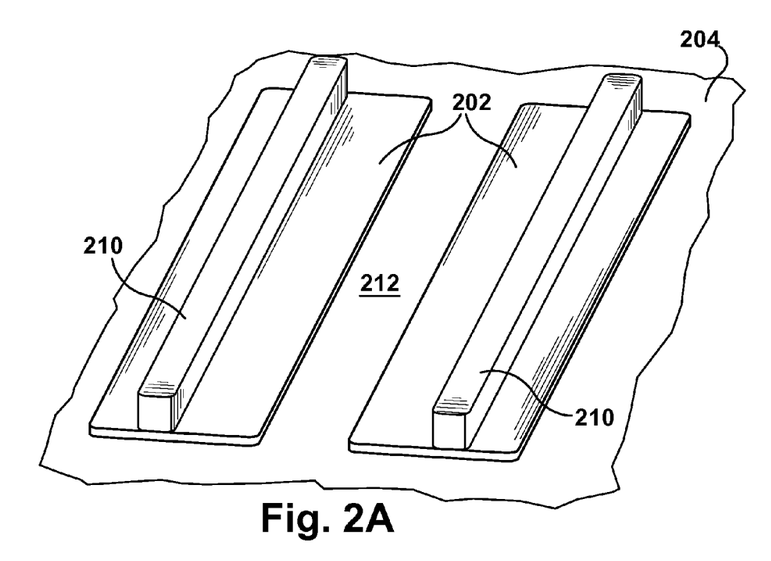
FIGS. 2A-2B are top views of a component of the embodiment of FIG. 1 in two example configurations.
Figure 2B:
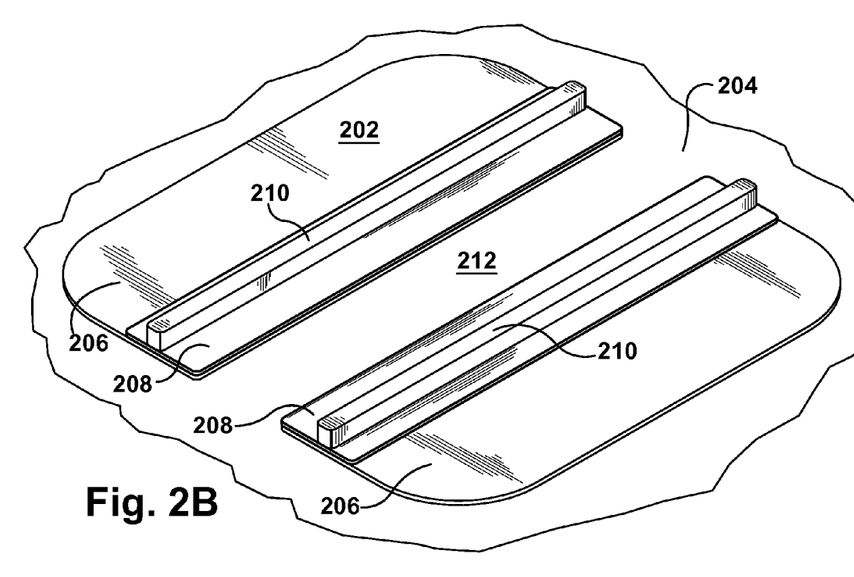

FIGS. 2A-2B depict different example configurations of a first component of the apparatus 100. A guiding substrate 202 (two shown) extends substantially parallel to a skin surface 204 and is selectively directly fastened thereto. For example, the guiding substrate 202 can have an adhesive backing (not shown) that sticks to a suitably prepared skin surface 204, may be sutured or otherwise anchored to the skin surface using a separate fastener (not shown), or may be fastened to the skin surface in any desired manner. The guiding substrate 202 shown in FIGS. 2A-2B is a substantially planar sheet of material and is adhered to the skin surface 204. In FIG. 2A, the guiding substrate 202 is substantially rigid. In FIG. 2B, each guiding substrate 202 includes a substantially flexible portion 206 and a substantially rigid portion 208. The arrangement of FIG. 2B may be helpful, for example, when the user wishes to stretch, deform, or otherwise manipulate the patient's skin surface 204 during the surgical procedure, since the substantially flexible portion 206 facilitates the ability of the guiding substrates 202 to remain pliable but still firmly and directly fastened to the skin surface 204 to support the other portions of the apparatus 100 for use. Optionally, some or all of the guiding substrates 202 could be removed and possibly replaced to facilitate various steps of the surgical procedure described below. For example, the substantially rigid portions 208 could be removed from the substantially flexible portions 206 to facilitate flexibility of the guiding substrates 202 during access through the skin and then replaced to return some degree of rigidity to the guiding substrates.

At least one guiding structure 210 is supported by a corresponding guiding substrate 202 in a substantially fixed relationship to an access site 212 of the skin surface 204. In FIGS. 2A-2B and similarly arranged Figures, the access site 212 is located substantially laterally between the two guiding substrates 202 in an interposed relationship. In the embodiment shown in the Figures, the guiding structures 210 are a pair of guiding rails 210 which are fastened to the skin surface 204 in a laterally spaced relationship. Here, the guiding rails 210 are arranged substantially parallel to one another (and to the skin surface 204), extending along the skin surface adjacent the access site 212 located therebetween, for interaction as described below with other components of the apparatus 100. In other words, one guiding rail 210 is located laterally to a first side (e.g., the left) of the access site 212 and the other guiding rail 210 is located laterally to a second side (e.g., the right) of the access site. Optionally, the guiding rails 210 may be located laterally equidistant from the access site 212 when the guiding substrates 202 are fastened to the skin surface 204. However, one or more guiding structures 210, having any desired configuration and spacing relative to each other and to the access site 212, can be provided by one of ordinary skill in the art for a particular application of the present invention. The guiding substrate(s) 202 and/or guiding structures 210 may be removed from the above-described use position at/near the access site 212 during at least a portion of the surgical procedure, optionally being replaced as described above toward the end of the surgical procedure once access through the skin surface 204 is no longer needed.

Figure 3A:
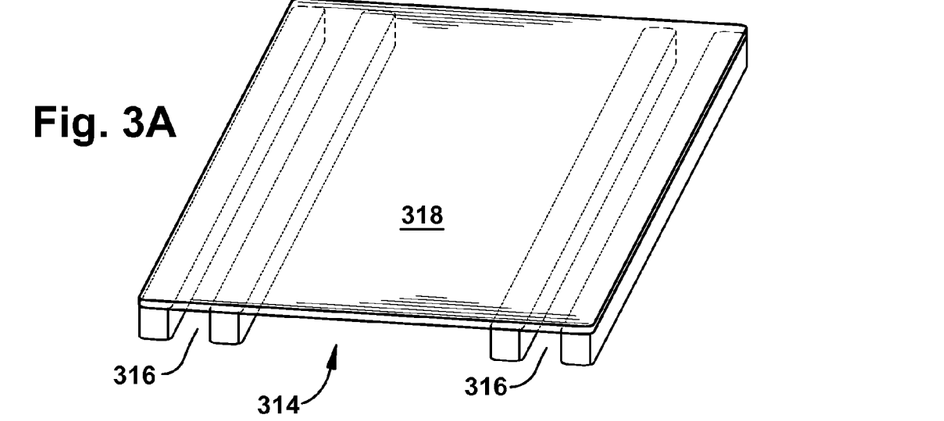
FIG. 3A is a perspective side view of a component of the embodiment of FIG. 1.
Figure 3B:
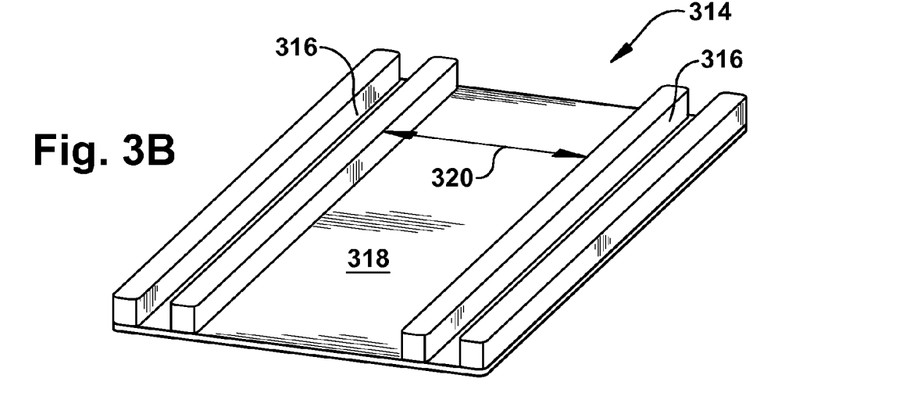
FIG. 3B is a bottom view of the component of FIG. 3A.
Figure 4:
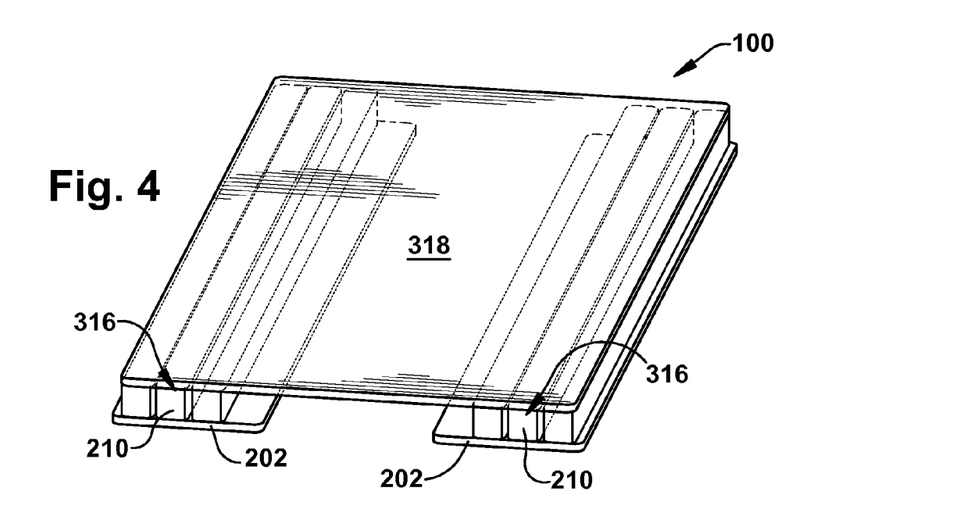
FIG. 4 is a perspective side view of the components of FIGS. 2A and 3A-3B in an example use configuration.

FIGS. 3A-3B depict top and bottom views, respectively, of a placement jig 314 according to an embodiment of the present invention. The placement jig 314 shown includes two jig channels 316 spaced a predetermined distance apart by a jig body 318. The placement jig 314 is selectively attachable (directly or indirectly) to the guiding substrates 202 for maintaining a substantially fixed relationship between the guiding substrates at a first spacing distance 320. Here, as shown in FIG. 4, the guiding rails 210 each mate with a jig channel 316. The term "mating" is used herein to indicate a relationship in which the contours of two structures are at least partially matched or coordinated in at least two dimensions. For example, both the guiding rails 210 and the jig channel 316 could have profiles that are—in any dimension thereof—protruding, retracted, concavely curved, convexly curved, planar/linear, or any combination of those or other profile shapes.

Optionally, the dimensions of the guiding rails 210 and jig channels 316 may be chosen such that the guiding rails are frictionally engaged with the jig channels. For example, when these structures are in the FIG. 4 arrangement, a user may be able to pick up and manipulate the placement jig 314 to place the guiding rails 210 (and attached guiding substrates 202) into a desired position without touching the guiding structures or rails 202 or 210 directly. Other means for engaging the placement jig 314 with a particular guiding substrate 202 (directly or via the guiding structure or another member) include magnetism, suction, static electricity, mechanical means (e.g., lifting peg/hole), or any other suitable engagement scheme.

Particularly when the guiding substrates 202 are attached to the skin surface 204 using adhesive on the underside of the guiding substrates, the placement jig 314 can be used to help position the guiding substrates 202 in a relatively precise and desirable manner, as compared to freehand placement. For example, the placement jig 314 and guiding rails 210 could be arranged as shown in FIG. 4 to place the guiding rails at a predetermined lateral neutral rail space distance (here, first spacing distance 320) relative to one another before the guiding rails are fastened to the skin surface 204, and the placement jig maintains that neutral rail space distance between the guiding rails during fastening of the guiding rails to the skin surface.

When the guiding substrates 202 are adhesively fastened to the skin surface 204, the placement jig 314 can hold the guiding rails 210 as shown in FIG. 4, the placement jig can be manipulated to bring the (adhesive) underside of the guiding substrates 202 into contact with the skin surface, and then the placement jig can be removed, leaving the guiding substrates and associated guiding rails fastened to the skin surface in the arrangement (spacing and relative orientation) shown in FIG. 1A. One of ordinary skill in the art can readily provide a placement jig 314 having any suitable configuration, able to contact and/or grasp any type of guiding structure, in any desired manner, for a particular application of the present invention. When used, the placement jig 314 can help to place one or more guiding substrates 202 and/or guiding structures into a desired position on the skin surface 204 at a predetermined absolute or relative location, and in a repeatable manner. Accordingly, use of the guiding structures as a "landmark" during the surgical procedure may be enhanced for certain use environments of the present invention, though the substantially fixed spacing relationship between the guiding structure and the access site will generally be present even without the use of the placement jig 314.

Figures 5A, 5B:
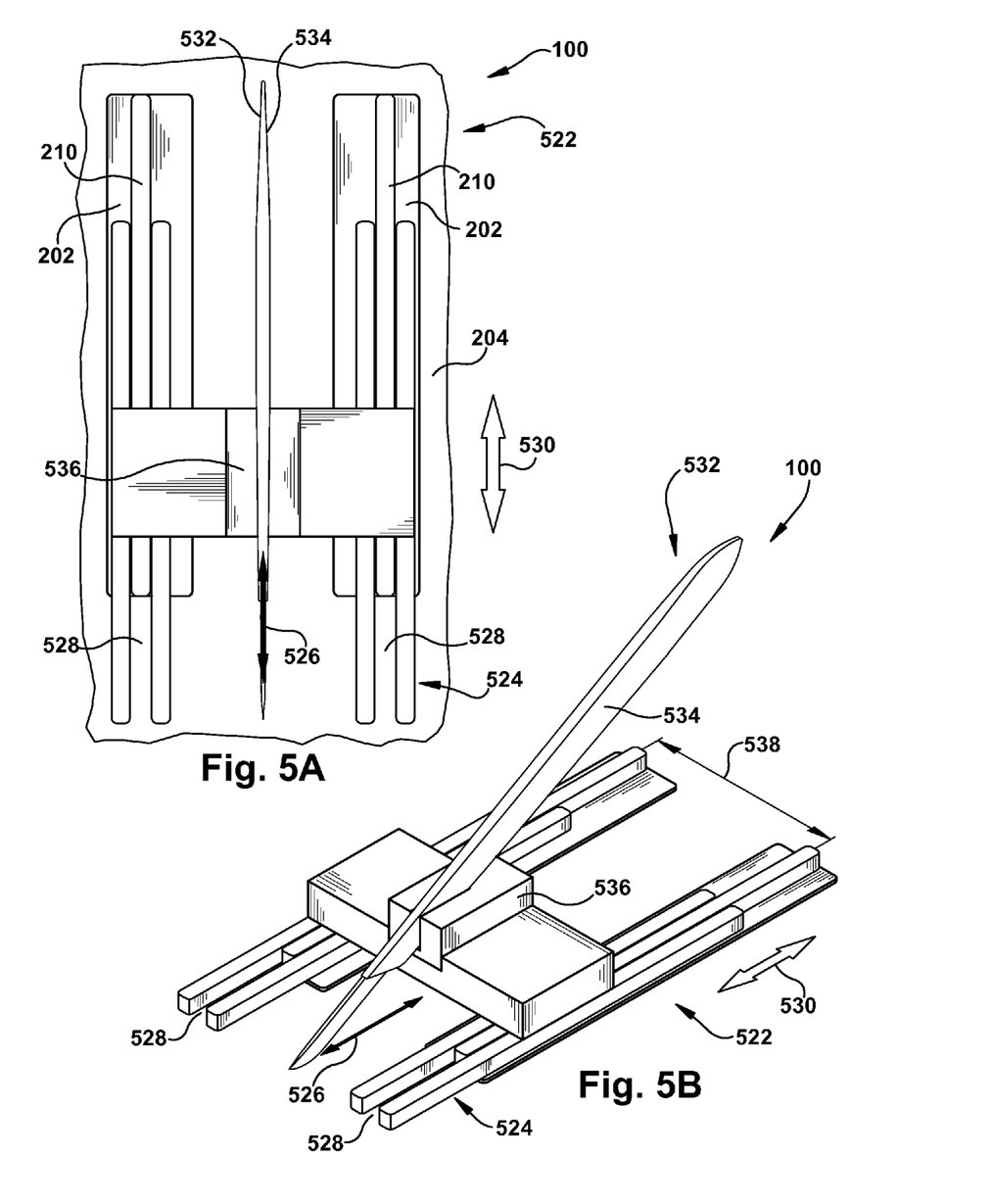
FIG. 5A is a top view of a component of the embodiment of FIG. 1.
FIG. 5B is a side view of the component of FIG. 5A.

Turning to FIGS. 5A-5B, the guiding rails 210 have already been fastened to the skin surface 204 at the first spacing distance 320. The access site 212 is interposed laterally between the guiding substrates 202. The apparatus 100 includes at least one tool carriage 522 having a following structure 524 which is configured for selective engagement with the guiding structure such that the tool carriage is guided along a predetermined action path 526 when the following structure and guiding structure are engaged and motive force is provided to the tool carriage. As shown in FIG. 5A, the depicted tool carriage 522 has a pair of following structures 524 which include following channels 528 configured for sliding engagement with the guiding rails 210 (omitted from FIG. 5B for clarity). Optionally, guiding rails 210 or other guiding structures could also or instead be provided (not shown) on a tool carriage 522 for engagement and interaction with a guiding substrate 202 in a manner similar to that described herein with reference to the guiding structure(s) provided on the guiding substrate.

Regardless of the way in which the guiding structure(s) and tool carriage(s) 522 are provided and configured, motive force exerted on the tool carriage 522 in the transverse direction 530 will cause the tool carriage to move, guided by engagement between the following channels 528 and the guiding rails 210, in the transverse direction. The action path 526 may be substantially linear, particularly when the guiding rails 210 are substantially linear, and may be transversely oriented across the skin surface 204 or may have any other desired configuration. For example, a longitudinally (i.e., perpendicular to the lateral skin surface) slanting action path 526 may be provided when the guiding rails 210 are thicker at one end than at the other—such a longitudinally slanting action path may be useful in providing a varying-depth incision. It is contemplated that, for many embodiments of the present invention, the three-dimensional spatial configuration of the action path 526 will bear a direct correspondence to at least a portion of the three-dimensional spatial configuration of the guiding structure.

The tool carriage 522 is configured to accept at least a chosen one of a plurality of surgical tools 532 for sequential interaction with the access site 212. For example, and as shown in FIGS. 5A-5B, the tool carriage 522 accepts a scalpel 534. As another incising option (not shown), the tool carriage 522 could accept just a blade of a scalpel 534, without the handle, a Bovie knife, a cutting laser, a cutting electrode, or any other incising tool. The tool(s) 532 may be stock surgical tools or may be at least partially custom-made and/or custom-configured for a particular use. The tool carriage 522 shown includes a tool grasper 536 which is configured to hold the scalpel 534. The tool grasper 536 may have any desired configuration for holding any desired tool 532, using any desired type of engagement (including, but not limited to, frictional, compression, adhesive, magnetic, or any other suitable engagement type or combination thereof) and may be readily provided by one of ordinary skill in the art for a particular application of the present invention.

A lateral width of the tool carriage 522 may be chosen to exert a force upon the skin surface 204 as desired by the user when the tool carriage and guiding structure 210 are engaged together and the guiding substrate 202 is fastened to the skin surface 204. For example, when the apparatus 100 includes attachment of two guiding rails 210 to the skin surface 204 at the first spacing distance 320 relative to one another, the lateral width of the tool carriage 522 may be chosen to pull the guiding rails 210 closer together than the first spacing distance (i.e., the tool carriage will exert compressive force on the skin surface through engagement between the guiding structure and the following structure 524). Similarly, the lateral width of the tool carriage 522 may be chosen to push the guiding rails 210 further apart than the first spacing distance (i.e., the tool carriage will exert tensile force on the skin surface through engagement between the guiding structure and the following structure 524), to a second spacing distance 538. The latter situation will be more common when the apparatus 100 is being used to guide an incising tool (e.g., a scalpel) along the action path 526 to create an incision in the skin surface 204.

That is, when a surgeon is creating a freehand incision in a patient's skin surface 204, the surgeon will manually spread/tension the skin surface with her thumb and fingers so that she is cutting a relatively taut surface. However, such manually applied tension is inherently variable and unrepeatable, both along and perpendicular to the action path 526. Using the apparatus 100, a predetermined and repeatable tension can be applied uniformly to the access site 212 (e.g., by placement of the guiding rails 210 at the second spacing distance 538) to assist the incising tool 532 (carried by the tool carriage 522) in creating a relatively uniform and controlled incision.

Suitable tension for application during travel of the incising tool carriage 522 along the action path 526 might be, for example, in the range of two hundred to fifteen hundred grams, and preferably five hundred grams, for certain applications of the present invention. One of ordinary skill in the art can readily configure/design an apparatus 100 having appropriate dimensions—e.g., lateral width of the tool carriage 522—to achieve a desired amount of laterally oriented tension on the skin surface 204 during use. The tool carriage 522 could also or instead have a variable width provided by, for example, a spring (not shown) bearing some physical relationship to the desired tension, such that the width of the tool carriage can vary under influence of the spring during travel along the action path 526 to maintain constant tensile force upon the guiding structure(s) and, by virtue of the above-described attachments, upon the skin surface 204. Another example of a variable-tension tool carriage 522 includes a structure (not shown) allowing the user to manually set and/or maintain a width of the tool carriage during use of the apparatus 100.

Regardless of whether tensioning or compressive force(s) are exerted by the process, during use of the tool carriage 522 of FIGS. 5A-5B with an incising tool 532 the tool carriage may be automatically and/or manually guided along the action path 526 by any desired motive force, including, but not limited to, a user's manual manipulation, a small motor, a mechanical linkage, or any other suitable force. When the tool carriage 522 carries an incising tool 532, a cutting or blade portion of the incising tool—such as the scalpel 534 shown in the Figures—is brought into penetrating contact with the access site 212 of the skin surface 204 to create a laterally elongate incision at the access site, and thereby provide access below the skin surface.

When used, a scalpel 534 (or any other suitable tool 532) can be positioned as desired with respect to the skin surface 204. For example, a #10 scalpel blade could be placed at a twenty- to thirty-degree angle with respect to the skin surface, while a #15 scalpel blade could be placed at a forty-five degree angle with respect to the skin surface. Similarly, the scalpel 534 could be positioned to penetrate any desired distance into the skin surface 204 at the access site 212, such as in the range of two to twenty millimeters deep. The depth of penetration is based upon skin thickness and a desired penetration depth may vary responsive to patient characteristics (e.g., body fat). The tool carriage 522 and/or tool grasper 536 may be selectively adjustable, before and/or during use, to change the relative relationship between the held/carried tool 532 and the skin surface 204 at the access site 212 as desired.

Figures 6A, 6B:
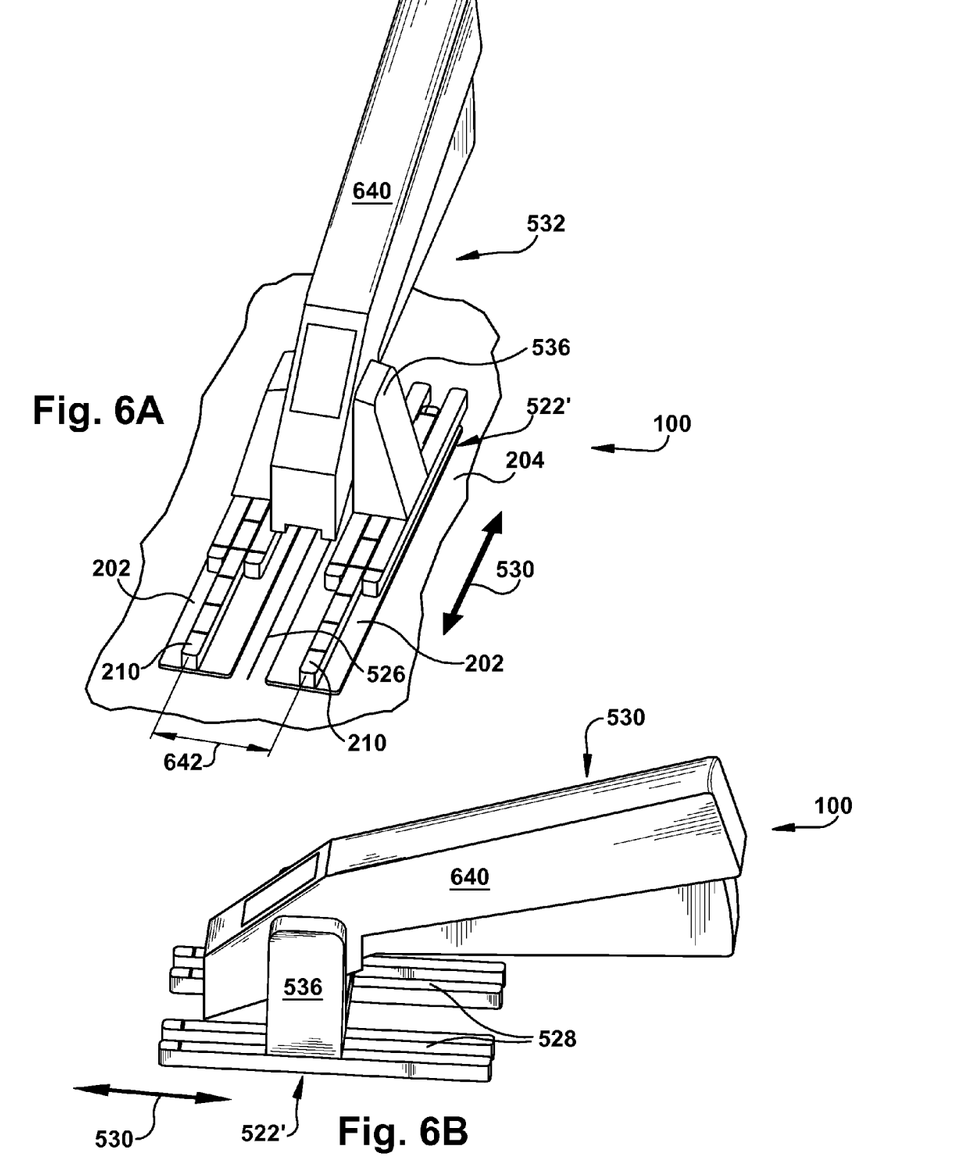
FIG. 6A is a top view of a component of the embodiment of FIG. 1.
FIG. 6B is a side view of the component of FIG. 6A.

FIGS. 6A-6B depict a tool carriage 522' which is configured to accept another type of surgical tool 532 than the tool carriage 522 of FIGS. 5A-5B. The tool 532 shown in combination with the tool carriage 522' of FIGS. 6A-6B is a closure tool, here a surgical stapler 640. While the tool carriage 522' could be the same tool carriage 522 as previously described, the tool grasper 536 shown in FIGS. 6A-6B differs from that of FIGS. 5A-5B, so the tool carriage 522' described with reference to FIGS. 6A-6B will be presumed to be a different one than that referenced in the above description of FIGS. 5A-5B.

As shown in FIGS. 6A-6B, the stapler 640 is carried by the tool carriage 522' similarly to the way that the previously described tool carriage 522 holds the scalpel 534. When motive power of any suitable type is provided to the apparatus 100, the tool carriage 522' is guided along the action path 526, which may coincide with the incision and/or the action path traveled by the previously described tool carriage 522. The stapler 640 is then actuated to substantially close the incision at the access site 212, thereby preventing access through the incision to the area below the skin surface 204.

As shown in FIGS. 6A-6B, the stapler 640 is configured to place a plurality of laterally spaced penetrating fasteners, such as staples, barbs, absorbable or nonabsorbable sutures, or the like, into the skin surface 204 to close the incision. As another alternative, a closure tool 532 using any suitable nonpenetrating fastener, such as liquid adhesive, adhesive strips, magnets, suction devices, or the like, could be used. The tool carriage 522' is placed into engagement with the guiding rails 210 through any suitable means, such as the depicted following channels 528. Any suitable motive force is applied to the tool carriage 522, directly or indirectly, to cause the stapler 640 to move in the transverse direction 530 along the action path 526. The stapler 640 or other closure tool 532 is actuated during this motion, continuously or at discrete intervals, to fasten the incision closed. Optionally, detents, a ratcheting structure, visible markings along the guiding rails 210, or any other aid may be provided to assist the user with automatically and/or manually actuating the stapler 640 at predetermined intervals during travel of the stapler 640 and associated tool carriage 422' along the guiding rails.

Optionally, a dimension, such as the lateral width, of the tool carriage 522' may be chosen to exert a desired direction and amount of force on the skin surface 204 during use of the apparatus 100. For example, it is well-known in the art that it is desirable to compress incision edges together during incision closure, such that the edges mutually evert and the dermal layers are brought firmly into contact and fastened/held in the everted configuration when the incision is closed, to facilitate wound healing. Accordingly, it will often be desirable for the tool carriage 522' to exert a laterally oriented compressive force on the skin surface 204 through engagement between the guiding and following structures when the guiding substrate(s) 202 are attached to the skin surface, similarly to the previously described tensioning of the skin surface during use of the apparatus 100. In the arrangement of FIGS. 6A-6B, the lateral width of the tool carriage 522' has been selected to pull the guiding rails 210 inward to a third spacing distance 642, which is narrower than the (neutral) first spacing distance 320, and thereby laterally compress the skin surface 204. However, the amount of compression on the skin surface 204 should be chosen to permit travel of the stapler 640 head along the action path 526 and to ensure that the inserted fasteners find sufficient purchase in the patient tissue.

Figure 7:
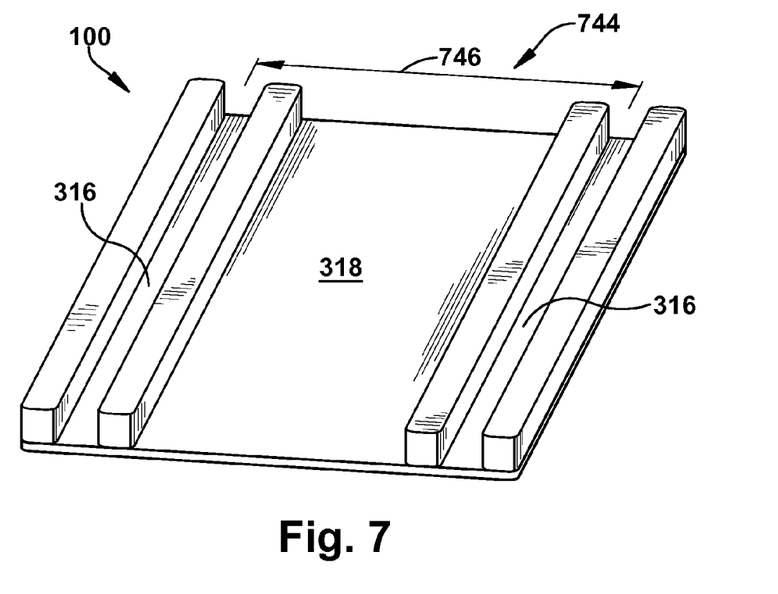
FIG. 7 is a top view of a component of the embodiment of FIG. 1.

Optionally, and as shown in FIG. 7, a maintenance jig 744 may be provided for postoperative use. The maintenance jig 744, like the placement jig 314, includes a jig body 316 and at least one structure, such as the depicted jig channels 316 for engaging a guiding substrate 202 and/or guiding rail 210. The maintenance jig 744 engages the guiding rails 210 (or other guiding structure) similarly to the way the placement jig 314 does, so that description will not be repeated here. When present, the maintenance jig 744 is attachable (directly or indirectly) to the guiding substrate(s) 202 for maintaining a substantially fixed relationship between two guiding substrates, or a guiding substrate and the skin surface 204, at a substantially laterally oriented fourth spacing distance 746, which may also be considered a "maintenance" distance. It is contemplated that, when a maintenance jig 744 is used, it will be configured for relatively long-term presence on the skin surface 204 to help facilitate healing.

The fourth spacing distance 746 may be smaller than the (laterally neutral) first spacing distance 320, in order to urge the guiding substrates 202 laterally closer together and thereby exert a laterally oriented compressive force on the skin surface 204 adjacent the access site 212 to hold the incision edges in the everted position during healing. When a maintenance jig 744 is provided after the incision has been made (and, optionally, closed by the closure tool 532), the maintenance jig may serve to hold the guiding rails 210 or any other structure(s) of the apparatus 100 in a predetermined relative distance, such any of the first through fourth spacing distances 320, 538, 642, or 746, as desired.

Figure 8:
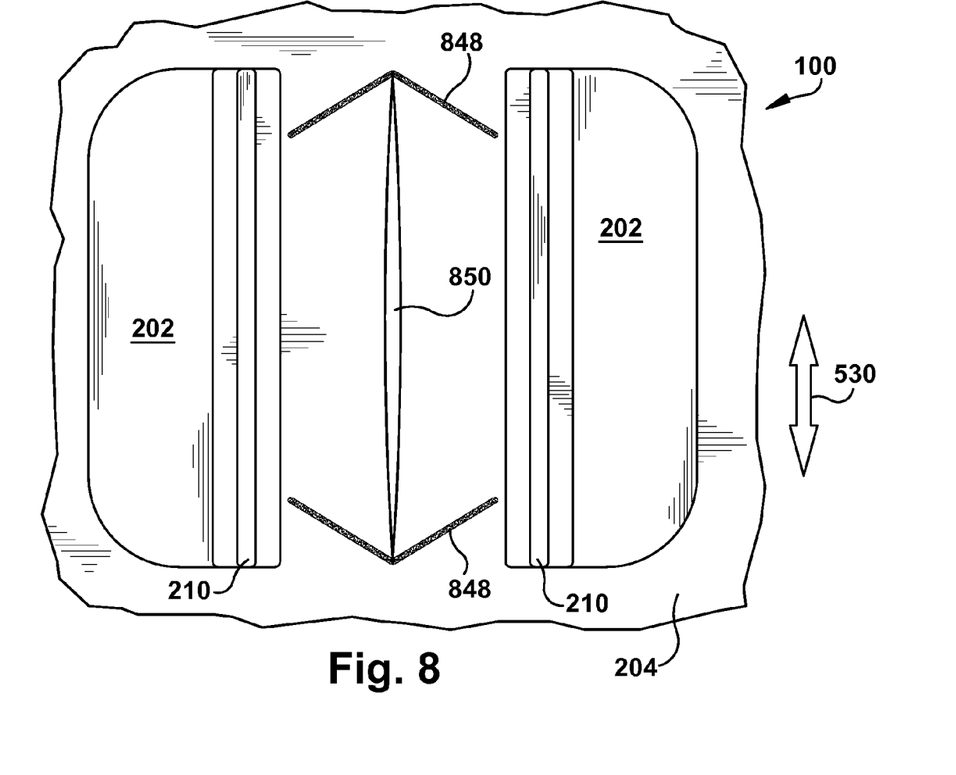
FIG. 8 is a schematic top view of a component of the embodiment of FIG. 1.

FIG. 8 depicts an optional configuration of the apparatus 100 wherein a pair of transverse stretchers 848 are provided at either end of the guiding rails 210. The stretchers 848 are fastened in any suitable manner (e.g., adhesives, barbs, sutures, or any other manner) to the access site 212 at or near the spaced-apart endpoints/apices of the incision 850. The stretchers 848 each have a substantially rigid, hinged structure with the hinge located at or near the incision. As the guiding rails 210 are brought closer together to exert a laterally compressive force on the skin surface 204, the hinges of the stretchers 848 move transversely away from the incision 850 to cause an "accordion" motion which exerts tension on the incision endpoints and thereby tensions the incision 850 and/or skin surface 204 in the transverse direction 530.

Figures 9, 10, 11:
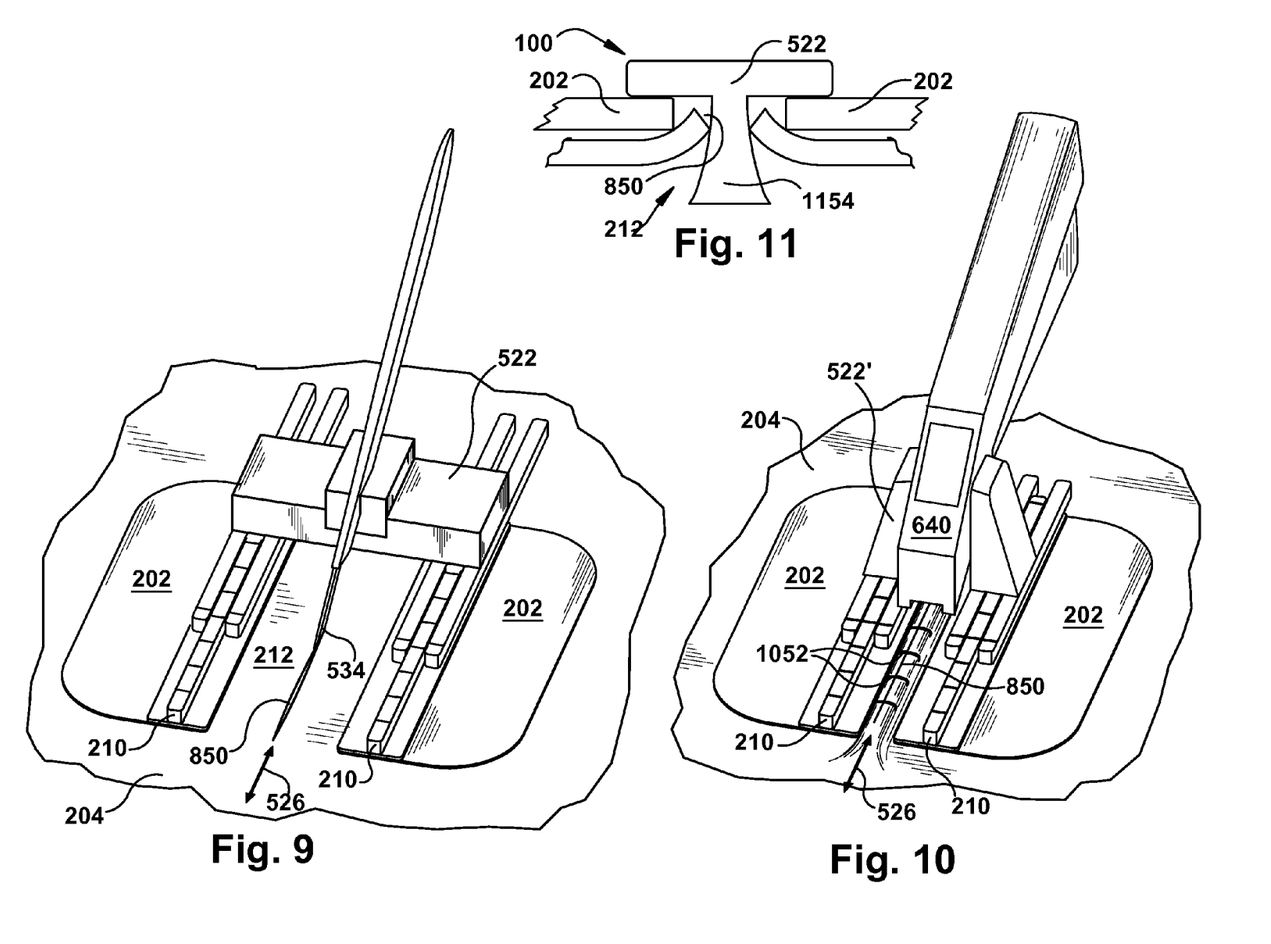
FIG. 9 is a top view of the component of FIGS. 5A-5B in an example use configuration.
FIG. 10 is a top view of the component of FIGS. 6A-6B in an example use configuration.
FIG. 11 is a schematic side view of a component of the embodiment of FIG. 1.

FIGS. 9-10 depict an example use sequence for an apparatus 100 according to an embodiment of the present invention. In FIG. 9, the guiding structures (here, guiding rails 210) have been placed in the desired locations with respect to the access site 212. The guiding substrates 202 have been directly fastened to the skin surface 204 to maintain the relative spacing between the guiding rails 210 and the access site 212. A first tool carriage 522, carrying a scalpel 534, has been placed into engagement with the guiding rails 210 and motive power supplied by the user's hands is causing motion of the first tool carriage 522 along the action path 526 to bring the scalpel into penetrating contact with the skin surface 204 and thereby make the incision 850. Optionally, the first tool carriage 522 lateral width has been chosen to laterally tension the skin surface 204 at the access site 212 (in the left-right direction, in this Figure). When the incision 850 has been made, the first tool carriage 522 is removed from the vicinity of the incision, and the guiding rails 210 remain. The surgical procedure requiring access through the incision 850 can then be performed.

In FIG. 10, the surgical procedure is complete and a second tool carriage 522' has been placed into engagement with the guiding rails 210. The second tool carriage 522' has a smaller lateral width than the first tool carriage 522, such that compressive force is laterally exerted—in the left-right direction, in this Figure—upon the skin surface 204 at the access site 212. As can be seen in FIG. 10, the compressive force has caused the skin surface 204 to elevate as the incision 850 edges at least partially evert under the influence of the compressive force. A plurality of staples 1052 have been placed, using the stapler 640 carried along the action path 526 by the second tool carriage 522', across the incision 850 and into penetrating contact with the skin surface 204 to close the wound. Downward pressure (perpendicular to the lateral plane) by the user on at least a portion of the apparatus 100 during incision 850 closure may also help to evert the incision edges in a desired manner.

In some cases, the incision 850 edges might fail to evert as desired under the compressive force or may even at least partially invert. In these cases, the user can manually evert at least a portion of the incision 850 edges, or the apparatus 100 may include any desired structure to help provide the described eversion. For example, FIG. 11 schematically shows a side view of the apparatus 100 in which a closing keel 1154 is carried by a tool carriage 522 along the length of the incision 850. The closing keel 1154 is shaped for interposition between the incision 850 edges to urge those edges upward into an everted position, as shown. The closing keel 1154 may be used sequentially or simultaneously with a stapler 640 or other portion of the apparatus 100.

Once the staples 1052 have been placed as desired, the second tool carriage 522' is removed from the vicinity of the closed incision 850. A maintenance jig 744 may then be placed across the access site 212 (optionally maintaining compression on the access site), and may remain in place as long as desired by the user. When present, the maintenance jig 744 may help to protect the fragile incision 850 area of the skin surface 204 from unwanted and potentially damaging contact with germs, other structures, or the like, and may also keep tension away from the incision 850 and decrease tissue motion at/near the access site 212. The maintenance jig 744 may also or instead help provide or maintain a supply of a medicament at the access site 212, to assist with wound healing. The maintenance jig 744 may also or instead have an absorbent feature to help capture fluids draining from the incision 850 during healing. When the guiding rails 210 are no longer needed—at the end of surgery or after a maintenance jig 744 is removed, for example—the guiding substrate (s) 202 can be removed from the skin surface 204 in any desired manner.

It is contemplated that a laparoscope port (not shown) could be provided to a tool carriage 522 such that the apparatus 100 holds the laparoscope port in a desired position with respect to an access site 212, such as by extending into the patient's body through the incision 850 in the skin tissue. Optionally, the incision 850 could be significantly larger in the lateral plane than is the laparoscope port; in this event, the incision may be at least partially closed around the laparoscope port, through use of the apparatus 100 or conventionally. The laparoscope port is then removed and the incision 850 closure completed at the end of the surgical procedure for which the laparoscopic access is desired. Through use of a laparoscope port, the user can avoid placing unwanted stress on the edges of the incision 850 during a surgical procedure.

It is also contemplated that, while the placement and maintenance jigs 314 and 744 are shown herein as relatively large, planar constructs, these components may instead be relatively narrow flexible or rigid strips, or have any other configuration relative to the guiding structures to perform the tasks described herein. For example, the guiding rails 210, or other type of guiding structure, could be manufactured integrally with a placement jig 314, which is then frangibly removed from the guiding rails once the guiding substrates 202 have been installed on the skin surface 204 as desired.

It is additionally contemplated that the closure tool 532 could be omitted from a particular use application of the present invention, particularly when a maintenance jig 744 is provided to hold the incision 850 edges together for healing without any additional incision-closure aids.

Further, it is contemplated here that a tool carriage 522 could act as a placement jig 314 and/or a maintenance jig 744, particularly when the tool carriage is not carrying a tool. The width of such a multi-purpose tool carriage could be adjustable (e.g., through the use of a spring-biased width-wise telescoping structure), to assist with providing the various spacing distances described herein.

It is also contemplated that the guiding rails 210 or other guiding structure may interact with other portions of the apparatus 100 (e.g., the tool carriage(s) 522) in a manner other than the sliding engagement shown. For example, any suitable structures of the apparatus 100 could be designed to include one or more wheels/rollers/spindles for rolling engagement, a "tank tread" type track for semi-rolling engagement, or any suitable guiding engagements or combinations thereof.

A "triggering" mechanism could be included to indicate when the tool carriage 522 has reached a predetermined location along the action path 526. The triggering mechanism could also or instead cause some type of action to occur (e.g., placement of staple, actuation of laser, or any other desired action) when the tool carriage 522 has reached a predetermined location along the action path 526. The triggering mechanism could be of any desired type such as, but not limited to, a cog on the tool carriage 522 engaging holes on the guiding substrate 202, a distance-measuring wheel on the tool carriage, a proximity sensor on any portion of the apparatus 100, or any other suitable type or combination of types.

Through use of the apparatus 100 described herein, a precisely placed incision 850 can be made. The precision of the incision 850 location, combined with the fixed and known distance(s) between the guiding structure(s) and the incision, is important to the functioning of the guided closure tool 532. Guidance of the closure tool 532 helps provide neat, efficient, and quick closure of the incision 850, all of which help with patient healing and achieving desirable surgical outcomes.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the apparatus 100 are merely illustrative; one of ordinary skill in the art could readily determine any number of tools, sequences of steps, or other means/options for placing the above-described apparatus, or components thereof, into positions substantively similar to those shown and described herein. Radiopaque markers could be placed in association with any of the described structures and components as desired. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications of the present invention. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. Though certain components described herein are shown as having specific geometric shapes, all structures of the present invention may have any suitable shapes, sizes, configurations, relative relationships, cross-sectional areas, or any other physical characteristics as desirable for a particular application of the present invention. The apparatus 100 may include a plurality of structures cooperatively forming any components thereof and temporarily or permanently attached together in such a manner as to permit relative motion (e.g., pivoting, sliding, or any other motion) therebetween as desired. While discrete fasteners are discussed herein, it is contemplated that fasteners connected to one another in any desired manner may also or instead be used with the present invention. The interaction between the guiding structure(s) and following structure(s) is described herein as being a slidable interaction, but any suitable means of interaction between the two types of structures (e.g., wheel on rail or any other desired type) may be provided for a particular use environment of the present invention, regardless of whether the means of interaction results in relative motion between the guiding and following structures during the guiding process. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. A system for facilitating access through a patient skin surface, the skin surface being substantially planar and laterally oriented, the system comprising:

a guiding substrate capable of extending substantially parallel to the skin surface and capable of being selectively directly fastened thereto, the guiding substrate, when fastened to the skin surface, supporting a guiding structure in a substantially fixed relationship to an access site of the skin surface;

a tool carriage configured to accept at least a chosen one of a plurality of surgical tools for sequential interaction with the access site, the tool carriage including a following structure configured for selective engagement with the guiding structure such that the tool carriage is guided along a predetermined action path when the following structure and guiding structure are engaged and motive force is provided to the tool carriage;

an incising tool, wherein the tool carriage is configured to be guided along the action path with the incising tool in penetrating contact with the access site of the skin surface to create a laterally elongate incision at the access site, and thereby provide access below the skin surface; and a closure tool, wherein the tool carriage is configured to be guided along the action path to substantially close the incision at the access site, using the closure tool, and thereby prevent access through the incision below the skin surface.

2. The system of claim 1, wherein the guiding substrate is a first guiding substrate, the guiding structure is a first guiding structure, and including a second guiding substrate capable of extending substantially parallel to the skin surface and capable of being selectively directly fastened thereto, the second guiding substrate, when fastened to the skin surface, supporting a second guiding structure in substantially fixed relationship to an access site of the skin surface.

3. The system of claim 2, including a placement jig attachable to the first and second guiding substrates for maintaining a substantially fixed relationship between the first and second guiding substrates at a first spacing distance.

4. The system of claim 3, including a maintenance jig attachable to the first and second guiding substrates for maintaining a substantially fixed relationship between the first and second guiding substrates at a maintenance spacing distance, the maintenance spacing distance being smaller than the first spacing distance, the placement jig being used before the surgical incision has been made at the access site and the maintenance jig being used after the surgical incision has been made at the access site.

5. The system of claim 4, wherein the maintenance spacing distance is selected to urge the first and second guiding substrates into exerting a laterally compressive force on the skin surface adjacent the access site when the first and second guiding substrates are fastened to the skin surface and the maintenance jig is attached to the first and second guiding substrates.

6. The system of claim 2, wherein, when the first and second guiding substrates are adhered to the skin surface, the first guiding structure is located laterally to a first side of the access site and the second guiding structure is located laterally to a second side of the access site, the first and second sides of the access site being laterally spaced from one another.

7. The system of claim 2, wherein, when the surgical tool is a closure tool, the tool carriage is configured to exert compressive force on the skin surface through engagement between the guiding structure and the following structure when the first and second guiding substrates are fastened to the skin surface, the compressive force acting to evert the edges of the incision such that the incision is closed by the closure tool with the edges held in the everted position.

8. The system of claim 2, wherein the first and second guiding substrates are located laterally equidistant from the access site when the first and second guiding substrates are fastened to the skin surface.

9. The system of claim 1, wherein the tool is at least one of a scalpel, a scalpel blade, a Bovie knife, a cutting laser, a cutting electrode, an incising tool, a closure tool, and a surgical stapler.

10. The system of claim 2, wherein a lateral width of the tool carriage is chosen to exert at least one of a tensile force and a compressive force on the skin surface through engagement between the guiding structure and the following structure when the first and second guiding substrates are capable of being fastened to the skin surface.

11. The system of claim 10, wherein a first tool carriage exerts tensile force on the skin surface when an incising tool is being guided along the action path and a second tool carriage exerts compressive force on the skin surface when a closure tool is being guided along the action path.

12. The system of claim 1, wherein the closure tool inserts a plurality of laterally spaced penetrating fasteners into the skin surface to close the incision.

13. The system of claim 1, wherein the action path is substantially linear and transversely oriented along the skin surface.

14. A method of facilitating access through a patient skin surface, the skin surface being substantially planar and laterally oriented, the method comprising the steps of:
directly fastening a guiding substrate to the skin surface, the guiding substrate extending substantially parallel to the skin surface;
supporting a guiding structure in a substantially fixed relationship to an access site of the skin surface with the guiding substrate;
providing a tool carriage configured to accept at least a chosen one of a plurality of surgical tools for sequential interaction with the access site, the tool carriage including a following structure;
selectively engaging the following structure with the guiding structure;
guiding the tool carriage along a predetermined action path when the following structure and guiding structure are engaged and motive force is provided to the tool carriage;
guiding the tool carriage, carrying a surgical tool which is an incising tool, along the action path with the incising tool in penetrating contact with the access site of the skin surface to create a laterally elongate incision at the access site, using the incising tool, and thereby provide access below the skin surface; and
guiding the tool carriage, carrying a surgical tool which is a closure tool, along the action path to substantially close the incision at the access site, using the closure tool, and thereby prevent access through the incision below the skin surface.

15. The method of claim 14, wherein the guiding substrate is a first guiding substrate and the guiding structure is a first guiding structure, and including the steps of:
directly fastening a second guiding substrate to the skin surface, the second guiding substrate extending substantially parallel to the skin surface; and
supporting a second guiding structure in a substantially fixed relationship to an access site of the skin surface with the second guiding substrate.

16. The method of claim 15, including the step of attaching a placement jig to the first and second guiding substrates for maintaining a substantially fixed relationship between the first and second guiding substrates at a first spacing distance.

17. The method of claim 16, including the steps of:
attaching a maintenance jig to the first and second guiding substrates for maintaining a substantially fixed relationship between the first and second guiding substrates at a maintenance spacing distance, the maintenance spacing distance being smaller than the first spacing distance;
using the placement jig before the surgical incision has been made at the access site; and
using the maintenance jig after the surgical incision has been made at the access site.

18. The method of claim 15, including the step of, when the first and second guiding substrates are fastened to the skin surface, choosing a lateral width of the tool carriage to exert at least one of a tensile force and a compressive force on the skin surface through engagement between the guiding structure and the following structure.

19. The method of 18, including the steps of:
exerting tensile force on the skin surface with a first tool carriage when an incising tool is being guided along the action path; and
exerting compressive force on the skin surface with a second tool carriage when a closure tool is being guided along the action path.

20. The method of claim 15, including the steps of:
exerting compressive force on the skin surface with the tool carriage through engagement between the guiding structure and the following structure when the first and second guiding substrates are fastened to the skin surface; and
everting the edges of the incision with the compressive force such that the incision is closed by the closure tool with the edges held in the everted position.

21. The method of claim 14, including the step of using the closure tool to insert a plurality of laterally spaced penetrating fasteners into the skin surface to close the incision.

22. A system for facilitating access through a patient skin surface, the skin surface being substantially planar and laterally oriented, the system comprising:
a pair of guiding rails capable of being fastened to the skin surface, the guiding rails being capable of being laterally spaced along the skin surface with an access site on the skin surface capable of being interposed laterally between the guiding rails;
at least one tool carriage configured to movably engage the guiding rails such that motive force exerted in the transverse direction upon the tool carriage causes the tool carriage to move, guided by the rails, in the transverse direction;
an incision tool selectively carried by a tool carriage and accordingly guided by the movable engagement between the tool carriage and the guiding rails to create a transversely extending incision in the skin surface at the access site and thereby provide access through the skin surface; and
a closure tool selectively carried by a tool carriage and accordingly guided by the movable engagement between the tool carriage and the guiding rails to close the incision in the skin surface at the access site and thereby substantially prevent access through the skin surface.

23. The system of claim 22, wherein the guiding rails are each substantially linear and are transversely oriented along the skin surface.

24. The system of claim 22, including a placement jig selectively engageable with the guiding rails, the placement jig being configured to place the guiding rails at a predetermined lateral neutral rail space distance relative to one another before the guiding rails are fastened to the skin surface, and the placement jig maintains that neutral rail space distance between the guiding rails during fastening of the guiding rails to the skin surface.

25. The system of claim 22, wherein the tool carriage that carries the incision tool is a first tool carriage and the tool carriage that carries the closure tool is a second tool carriage.

26. The system of claim 25, wherein the first tool carriage is dimensioned to urge the guiding rails to a predetermined lateral tensing rail space distance and thereby exert tensile force on the skin surface during creation of the incision.

27. The system of claim 25, wherein the second tool carriage is dimensioned to urge the guiding rails to a predetermined lateral compressing rail space distance and thereby exert compression force on the skin surface during closure of the incision.

28. The system of claim 27, wherein the compression force at least partially everts the edges of the incision together and the closure tool closes the incision with the edges held in the everted position.

29. The system of claim 22, wherein the closure tool inserts a plurality of laterally spaced penetrating fasteners into the skin surface to close the incision.

30. The system of claim 22, including a maintenance jig selectively engageable with the guiding rails, the maintenance jig being configured to place the guiding rails at a selected one of a predetermined lateral neutral rail space distance and a predetermined lateral compressing rail space distance relative to one another after the incision has been closed, and the maintenance jig maintaining that selected rail space distance between the guiding rails after conclusion of the surgical procedure for which access through the skin surface was provided by the incision at the access site.

31. A method of facilitating access through a patient skin surface, the skin surface being substantially planar and laterally oriented, the method comprising the steps of:
directly fastening a first guiding substrate to the skin surface, the first guiding substrate extending substantially parallel to the skin surface;
supporting a first guiding structure in a substantially fixed relationship to an access site of the skin surface with the first guiding substrate;
directly fastening a second guiding substrate to the skin surface, the second guiding substrate extending substantially parallel to the skin surface;
supporting a second guiding structure in a substantially fixed relationship to an access site of the skin surface with the second guiding substrate;
attaching a placement jig to the first and second guiding substrates for maintaining a substantially fixed relationship between the first and second guiding substrates at a first spacing distance;
attaching a maintenance jig to the first and second guiding substrates for maintaining a substantially fixed relationship between the first and second guiding substrates at a maintenance spacing distance, the maintenance spacing distance being smaller than the first spacing distance;
providing a tool carriage configured to accept at least a chosen one of a plurality of surgical tools for sequential interaction with the access site, the tool carriage including a following structure;
selectively engaging the following structure with the first guiding structure;
guiding the tool carriage along a predetermined action path when the following structure and first guiding structure are engaged and motive force is provided to the tool carriage;
when the surgical tool is an incising tool, guiding the tool carriage along the action path with the incising tool in penetrating contact with the access site of the skin surface to create a laterally elongate incision at the access site, using the incising tool, and thereby provide access below the skin surface;
using the placement jig before the surgical incision has been made at the access site;
using the maintenance jig after the surgical incision has been made at the access site; and
when the surgical tool is a closure tool, guiding the tool carriage along the action path to substantially close the incision at the access site, using the closure tool, and thereby prevent access through the incision below the skin surface.

32. The method of claim 31, including the step of, when the first and second guiding substrates are fastened to the skin surface and the maintenance jig is attached to the first and second guiding substrates, urging the first and second guiding substrates with the maintenance jig into exerting a laterally compressive force on the skin surface adjacent the access site.

* * * * *